(12) United States Patent  (10) Patent No.: US 8,653,257 B2
Brown et al.  (45) Date of Patent: Feb. 18, 2014

(54) DIBENZOTHIAZEPINE DERIVATIVES AND USES THEREOF—424

(75) Inventors: Dean Brown, Wilmington, DE (US); James R. Damewood, Wilmington, DE (US); Phil Edwards, Wilmington, DE (US); James Hulsizer, Wilmington, DE (US); James Campbell Muir, Macclesfield (GB); M. Edward Pierson, Jr., Wilmington, DE (US); Ashokkumar Bhikkappa Shenvi, Wilmington, DE (US); Steven Wesolowski, Wilmington, DE (US); Dan Widzowski, Wilmington, DE (US); Michael Wood, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 39 days.

(21) Appl. No.: 13/445,347

(22) Filed: Apr. 12, 2012

(65) Prior Publication Data

US 2012/0202991 A1 Aug. 9, 2012

Related U.S. Application Data

(63) Continuation of application No. 12/487,725, filed on Jun. 19, 2009, now Pat. No. 8,158,618.

(60) Provisional application No. 61/074,417, filed on Jun. 20, 2008.

(51) Int. Cl.
A61P 25/00 (2006.01)
A61K 31/554 (2006.01)
C07D 281/02 (2006.01)

(52) U.S. Cl.
USPC ........................................................ 540/551

(58) Field of Classification Search
USPC ........................................................ 540/551
See application file for complete search history.

(56) References Cited

U.S. PATENT DOCUMENTS

| | | | |
|---|---|---|---|
| 3,412,193 A | 11/1968 | Coppola | |
| 3,444,169 A | 5/1969 | Howell et al. | |
| 3,539,573 A * | 11/1970 | Hunziker et al. ............. | 540/551 |
| 3,546,226 A | 12/1970 | Schmutz et al. | |
| 3,683,034 A | 8/1972 | Doering et al. | |
| 3,758,479 A | 9/1973 | Schmutz et al. | |
| 3,852,446 A | 12/1974 | Schmutz et al. | |
| 3,884,920 A | 5/1975 | Schmutz et al. | |
| 3,908,010 A | 9/1975 | Schmutz et al. | |
| 3,962,248 A | 6/1976 | Schneider | |
| 4,879,288 A | 11/1989 | Warawa et al. | |
| 5,344,828 A | 9/1994 | Sawanishi et al. | |
| 5,750,566 A | 5/1998 | Monn et al. | |
| 6,897,206 B2 | 5/2005 | Sackeyfio et al. | |
| 6,955,815 B2 | 10/2005 | Sackeyfio et al. | |
| 7,335,371 B2 | 2/2008 | Sackeyfio et al. | |
| 7,491,715 B2 | 2/2009 | Ek et al. | |
| 7,491,871 B2 | 2/2009 | Eby | |
| 8,158,618 B2 * | 4/2012 | Brown et al. ............. | 514/211.13 |
| 2004/0224942 A1 | 11/2004 | Weiner et al. | |
| 2004/0266792 A1 | 12/2004 | Yelle | |
| 2006/0063754 A1 | 3/2006 | Edgar et al. | |
| 2006/0217366 A1 | 9/2006 | Davis et al. | |

FOREIGN PATENT DOCUMENTS

| | | |
|---|---|---|
| CH | 422793 | 4/1967 |
| CH | 476753 | 8/1969 |
| EP | 0447857 | 9/1991 |
| EP | 0282236 B1 | 12/1991 |
| FR | 1508536 | 1/1968 |
| GB | 980853 | 1/1965 |
| GB | 1164360 | 9/1969 |
| GB | 1042634 | 9/1996 |
| JP | 05-65257 | 3/1993 |
| NL | 294355 | 4/1965 |
| NL | 293201 | 7/1965 |
| RU | 2006126720 | 1/2008 |
| SU | 457220 | 11/1975 |
| WO | WO9606098 | 2/1996 |
| WO | WO9618621 | 6/1996 |
| WO | WO9723466 | 7/1997 |
| WO | WO9730998 | 8/1997 |

(Continued)

OTHER PUBLICATIONS

Burki, H.R. et al., "Effects of clozapine and other dibenzo-epines on central dopaminergic and cholinergic systems", Arzneim-Forsch (Drug Res.), 1977, vol. 27 (No. II), pp. 1561-1565.

Goldstein, J., "Quetiapine fumarate (Seroquel®): A New Atypical Antipsychotic", 35(3), Drugs of Today, 193-210 (1999).

Mandriolo, R., et al., "HPLC Analysis of the Novel Antipsychotic Drug Quetiapine in Human Plasma", Journal of Pharmaceutical and Biomedical Analysis, 2002, vol. 30, pp. 969-977.

Morse, J.L., et al., Abstract and 15 slides presented as a poster presentation: "The Disposition and Metabolism of Seroquel TM (ICI204,636), in Rat, Dog, Monkey and Man", Presented at Intl. Soc. Study Xenobiotics, 1995.

(Continued)

*Primary Examiner* — Brenda Coleman

(74) *Attorney, Agent, or Firm* — Ropes & Gray LLP

(57) ABSTRACT

Compounds the following formula:

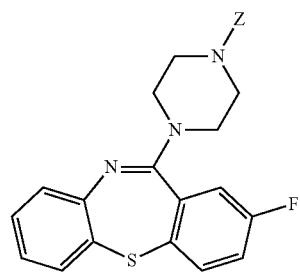

wherein Z is as described in the specification, pharmaceutically acceptable salts thereof, compositions comprising the same, and methods of treating bipolar disorder, an anxiety disorder, a mood disorder or schizophrenia or other psychotic disorder with said compounds.

3 Claims, No Drawings

(56) References Cited

FOREIGN PATENT DOCUMENTS

| | | |
|---|---|---|
| WO | WO9903859 | 1/1999 |
| WO | WO9905134 | 2/1999 |
| WO | WO0042044 | 7/2000 |
| WO | 0108680 A1 | 2/2001 |
| WO | WO0129034 | 4/2001 |
| WO | WO0208212 | 1/2002 |
| WO | WO0296912 | 5/2002 |
| WO | 0243652 A2 | 6/2002 |
| WO | 02060870 | 8/2002 |
| WO | WO02094794 | 11/2002 |
| WO | 03006026 A1 | 1/2003 |
| WO | 03026563 A2 | 4/2003 |
| WO | WO03087102 | 10/2003 |
| WO | WO03087103 | 10/2003 |
| WO | WO03087104 | 10/2003 |
| WO | WO2004016616 | 2/2004 |
| WO | WO2004016617 | 2/2004 |
| WO | WO2004019947 | 3/2004 |
| WO | 2004026030 A2 | 4/2004 |
| WO | 2004056182 A1 | 7/2004 |
| WO | 2004076431 A1 | 9/2004 |
| WO | 2004078216 A2 | 9/2004 |
| WO | WO2004092135 | 10/2004 |
| WO | 2005012274 A1 | 2/2005 |
| WO | WO2005063254 | 7/2005 |
| WO | 2005092392 A2 | 10/2005 |
| WO | WO2006071730 | 7/2006 |
| WO | WO2006073360 | 7/2006 |
| WO | WO2006107948 | 10/2006 |
| WO | WO2007053618 | 5/2007 |
| WO | 2008079847 A1 | 7/2008 |
| WO | WO2008100715 | 8/2008 |
| WO | WO2008150232 | 12/2008 |
| WO | WO2008150233 | 12/2008 |

OTHER PUBLICATIONS

Mutschler, E., "Arzneimittelwirkungen", Wissenschaftziche Verlagsgesellschaft, Stuttgart, XP002298363, p. 127, 1991, Paragraph entitled "Indikationen".

Schmutz, J., "Neuroleptic Piperazinyl-dibenzo-azepines chemistry and structure-activity relationships", Arzneim-Forsch. (Drug Res.), 1975, vol. 25, (No. 5), pp. 712-720.

Schmutz, J., "Chance and Design in Drug Research, Explained using Tricyclic Psychoactive Drugs as the Example", Pharmaceutica Acta Helvetiae, 1972, vol. 48 (No. 3), pp. 117-132.

Schmutz, J., et al., "Chemical constitution and pharmacological action of a new neuroleptic tricyclic group", Chimie Therapeutique, Nov.-Dec. 1967, No. 6, pp. 424-429.

Warawa, E.J., et al., "Behavioral Approach to Nondyskinetic Dopamine antagonists: Identification of Seroquel", J. Med. Chem, 2001, vol. 44, pp. 372-389.

USFDA Website; CDER Archives, New Drug Approval Packages, New Drug Approvals, 1997, (http://www.fda.gov/cdr/foi/nda/index97.htm) for Seroquel (Quetiapine Fumarate Tablets): Pharmacology Review(s) Part A, p. 14, Table 67, Posted May 12, 1998; Review & Evaluation of Pharmacology & Toxicology Data.

Marilyn A. Davis, et al., "The highly efficacious actions of N-desmethylclozapine at muscarinic receptors are unique and not a common property of either typical or atypical antipsychotic drugs: Is M1 agonism a pre-requisite for mimicking clozapine's actions?", Psychopharmacology (2005) 178: pp. 451-460.

Jeffrey A. Lieberman, et al, "Quetiapine Fumarate: A 5-Year Review", Journal of Clinical Psychiatry, Supplement 13, vol. 63, 2002, pp. 1-38.

Topham, J.C., et al., "Marketing Authorization Application for Seroquel TM (Quetiapine, ICI 204, 636)," Expert Report on the Pharmaco-Toxicological (pre-clinical) Documentation, dated Jul. 24, 1996, (Section 2.4 and Table C42), Extracted information from an AstraZeneca internal report for regulatory submission.

Weiden, P., et al., "Atypical antipsychotic drugs and long-term outcome in schizorphrenia", J. Clinical Psychiatry, (1996);57 (suppl 11), pp. 53-60.

Helen R. Winter, et al, "Steady-State Pharmacokinetic, Safety, and Tolerability Profiles of Quetiapine, Norquetiapine, and Other Quetiapine Metabolites in Pediatric and Adult Patients with Psychotic Disorders", Journal of Child and Adolescent Psychopharmacology, vol. 18, No. 1, 2008: pp. 81-96.

C. Devane, et. al., "Clinical Pharmacokinetics of Quetiapine: An Atypical Antipsychotic", Clinical Pharmacokinetics, 2001, vol. 40, No. 7 pp. 509-522.

Muramatsu, et al., "[Studies on zwitter-ionization of drugs. I. Synthesis and pharmacological activities of N-alkylcarboxylic acid derivatives of 4-(2-chlorodibenz-[b,f] [1,4]oxazepin-11-yl)piperazine, 4-(2-chlorodibenzo[b,f]-[1,4]thiazepin-11-yl)piperazine, and 4-(11H-dibenz-[b,e]azepin-6-yl)piperazine]", Yakugaku Zasshi (1992) 112(7): pp. 479-488.

Burki, et al., "Dibenzo-epines; Effect of the basic side-chain on neuroleptic activity", Eur J. Med Chem—Chimica Therapeutica, Sep.-Oct. 1978 13(5): pp. 479-485.

Gauch, et al., "The metabolism of 2-chloro-11-(4-methyl-1-piperazinyl)dibenzo-[b,f][1,4]-thiazepine (clotiapine)", Farmaco (1968) 24(2), pp. 100-109.

Caley, et al., "Focus on quetapine: The fourth atypical antipsychotic", Formulary (1998) 33(2), pp. 105-106, 109-110, 112, 115-116 and 119.

Schmutz, J, et al., "Neue Synthese von Lactamen der Dibenz[b,f]-1, 4-thiazepin-oxazepin and Dibenz[b,e]-azepin-Reihe", Helvetica Chimica ACTA, vol. 48, Fasciculus 2 (1965)—No. 38, pp. 336-347. Neuroleptics, pp. 125-130, 1991.

* cited by examiner understand

DIBENZOTHIAZEPINE DERIVATIVES AND USES THEREOF—424

This application is a continuation application of U.S. patent application Ser. No. 12/487,725, filed Jun. 19, 2009 (now U.S. Pat. No. 8,158,618), which claims the benefit of U.S. provisional application 61/074,417, filed Jun. 20, 2008.

FIELD OF THE INVENTION

The present invention relates to methods of treating bipolar disorders, mood disorders, anxiety disorders, and schizophrenia and other psychotic disorders, and to compounds suitable for use in such treatments, pharmaceutically acceptable salts thereof, pharmaceutical compositions comprising the such compounds, processes for preparing the such compounds and prodrugs thereof.

BACKGROUND OF THE INVENTION

A number of drugs have been approved to treat bipolar disorder and schizophrenia (e.g., anticonvulsants and atypical antipsychotics), and treatment of mania has been achieved with several atypical antipsychotics (e.g., risperidone, olanzapine and quetiapine). Other compounds have been used for the clinical treatment of major depressive disorder (e.g., reboxetine and desipramine) as well as bipolar depression (quetiapine). However, improvement in therapy is still desired in terms of achieving better remission rates, more effective treatment of depression and an improved side-effect profile (e.g., reduced sedation and reduced weight gain).

For nearly 50 years, since the early 1960s, scientific and clinical investigators have sought to understand the pharmacology of tricyclic neuroleptic compounds. Numerous US and Foreign patents and scientific publications have described hundreds of different tricyclic compounds with varying antipsychotic and anti-depressive properties. In the 1960s, CH422793 a Swiss patent filed in 1961, and NL293210 a Dutch patent application filed in 1963, described tricyclic compounds. Almost forty years later, a scientific paper published in 2001 (Behavioral Approach to Nondyskinetic Antagonists: Identification of Seroquel, J. Med. Chem. 2001, 44, 372-380) described other different tricyclic compounds. Still more recently in early 2009, U.S. Pat. Nos. 7,491,715 B1 and 7,517,871 B1 were granted describing new analogues of clozapine.

Despite having a wide spectrum of pharmacological activity, current bipolar and schizophrenia drugs exhibit variable efficacy and side-effect profiles. Although some current drugs have acute efficacy, remission rates are still low. Safety and tolerability are still issues since approximately 75% of patients experience side effects, and treatment compliance is a major issue. Additionally, the mechanism of action of atypical antipsychotics is not well understood, for example, the label of Seroquel states:

"the mechanism of action of Seroquel, as with other drugs having efficacy in the treatment of schizophrenia and acute manic episodes associated with bipolar disorder, is unknown. However, it has been proposed that this drug's efficacy in schizophrenia is mediated through a combination of dopamine type 2 (D2) and serotonin type 2 (5HT2) antagonism. Antagonism at receptors other than dopamine and 5HT2 with similar receptor affinities may explain some of the other effects of Seroquel. Seroquel's antagonism of histamine H1 receptors may explain the somnolence observed with this drug. Seroquel's antagonism of adrenergic α1 receptors may explain the orthostatic hypotension observed with this drug."

Similarly, the label for olanzapine states:

"The mechanism of action of olanzapine, as with other drugs having efficacy in schizophrenia, is unknown. However, it has been proposed that this drug's efficacy in schizophrenia is mediated through a combination of dopamine and serotonin type 2 (5HT2) antagonism. The mechanism of action of olanzapine in the treatment of acute manic episodes associated with Bipolar I Disorder is unknown.

Antagonism at receptors other than dopamine and 5HT2 with similar receptor affinities may explain some of the other therapeutic and side effects of olanzapine. Olanzapine's antagonism of muscarinic M1-5 receptors may explain its anticholinergic effects. Olanzapine's antagonism of histamine H1 receptors may explain the somnolence observed with this drug. Olanzapine's antagonism of adrenergic α1 receptors may explain the orthostatic hypotension observed with this drug."

Thus, notwithstanding that numerous tricyclic compounds having antipsychotic and anti-depressant activity have been described and used in therapy, improved ways to treat schizophrenia and bipolar disease are still sought. Particularly, effective treatment of the depressive phase of bipolar disorder is desired and still sought, as is treatment of the manic phase, mood stabilization and maintenance for sufferers of bipolar disorder.

DESCRIPTION OF THE INVENTION

We contemplate a new target product efficacy profile that is consistent with the putative mechanisms of action of quetiapine in bipolar disorder (i.e. potent NET inhibition and moderate D2 antagonism). Clinical studies with quetiapine suggest that NET and D2 occupancy in the range of 30 to 60% may be sufficient to drive a therapeutic effect in bipolar disorder. Further, improved safety may be achieved by having less interaction with other targets (e.g., H1, M1) at clinical doses achieving 50% NET occupancy.

A therapeutic agent with such a profile is expected to provide advantages for the treatment of the depressive phase of bipolar disorder, to have potential for mood stabilization and maintenance of sufferers of bipolar disorder with potential for use in the amelioration of mania associated with bipolar conditions.

Thus, in one aspect, it is desirable to obtain at least one of the following attributes: moderate D2 antagonism; potent NET inhibition; or an H1 in vitro binding $K_i$ value that is close to the value of the $K_i$ for NET. In a particular aspect it is desirable to obtain at least one of the following in vitro attributes: D2 GTPγS $IC_{50}$ less than about 600 nM; D2 binding $K_i$ less than about 200 nM; NET inhibition $K_i$ less than about 50 nM; or H1 that has a $K_i$ in the range of about at least half the value of the $K_i$ for NET to greater than the $K_i$ for NET.

In another aspect, it is desirable to identify a compound having potent inhibition of the norepinephrine transporter (NET), moderate D2 receptor antagonism and reduced affinity at secondary targets (e.g., H1, M1) relative to NET.

In a more particular aspect, it is desirable to identify a compound with potent NET inhibition (uptake $K_i$<50 nM) moderate D2 antagonist potency (GTPγS $IC_{50}$<500 nM) and H1 Ki equivalent to or less than NET Ki.

We have identified and herein describe a compound, 2-fluoro-11-piperazin-1-yl-dibenzo[b,f][1,4]thiazepine, that has not been previously described, having the desirable properties described above.

Thus, a pharmacologically active compound 2-fluoro-11-(piperazin-1-yl)dibenzo[b,f][1,4]thiazepine, pharmaceutically acceptable salts thereof, prodrugs thereof, compositions containing the compound, a prodrug or a pharmaceutically acceptable salt thereof and methods of treating bipolar disorder and schizophrenia with the compound, a prodrug or a pharmaceutically acceptable salt thereof are described herein.

Thus, provided herein is a compound of Formula I:

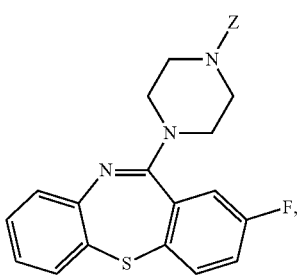

I or a pharmaceutically acceptable salt thereof, wherein Z is H, —C(=O)—$R^1$, —C(=O)$OR^1$, —C(=O)$OCH_2$, —CH($R^1$)—NHC(=O)$R^2$, —C(=O)$OCHR^2OC$(=O)$R^3$, —$CR^1$=$CR^2$ or —CH=CHC(=O)$R^4$, wherein $R^1$, $R^2$, $R^3$ and $R^4$ are each independently at each occurrence alkyl, cycloalkyl, aryl, heteroaryl or heterocycloalkyl or are as further described herein.

Also provided herein is at least one composition comprising a compound of Formula I, or a pharmaceutically acceptable salt thereof. In some embodiments, the compositions comprise a pharmaceutically acceptable carrier, diluent or excipient.

Further provided herein are methods for treating psychiatric disorders comprising administering to a mammal a therapeutically effective amount of a compound of Formula I, or a pharmaceutically acceptable salt thereof. Particularly, provided herein are methods for treating psychiatric disorders comprising administering to a mammal a therapeutically effective amount of a compound of Formula II

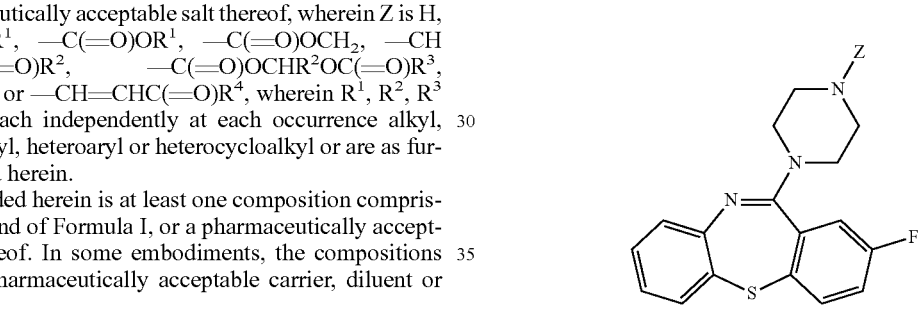

II or a pharmaceutically acceptable salt thereof.

Yet further provided herein are methods of treating bipolar disorder, mood disorders, schizophrenia and other psychotic disorders, or anxiety disorders, comprising administering to a subject a therapeutically effective amount of a compound of Formula I or Formula II, or a pharmaceutically acceptable salt thereof. Particularly, provided herein are methods of treating bipolar disorder, a mood disorder, schizophrenia and other psychotic disorders, or anxiety disorder, comprising administering to a subject a therapeutically effective amount of a compound of Formula II, or a pharmaceutically acceptable salt thereof.

Still yet further provided herein is a compound of Formula I or Formula II, or a pharmaceutically acceptable salt thereof, for use in treating schizophrenia and other psychotic disorders, an anxiety disorder, and/or a mood disorder.

Additionally provided herein is a compound of Formula I or Formula II, or a pharmaceutically acceptable salt thereof, for use in the manufacture of a medicament for the treatment of schizophrenia and other psychotic disorders, bipolar disorder, an anxiety disorder, and/or a mood disorder.

Still yet additionally provided herein are processes for preparing compounds of Formula I or Formula II, and pharmaceutically acceptable salts thereof; intermediates useful for the preparation of such compounds and processes for preparing and using such intermediates.

DETAILED DESCRIPTION OF EMBODIMENTS

Provided herein are compounds of Formula I:

I

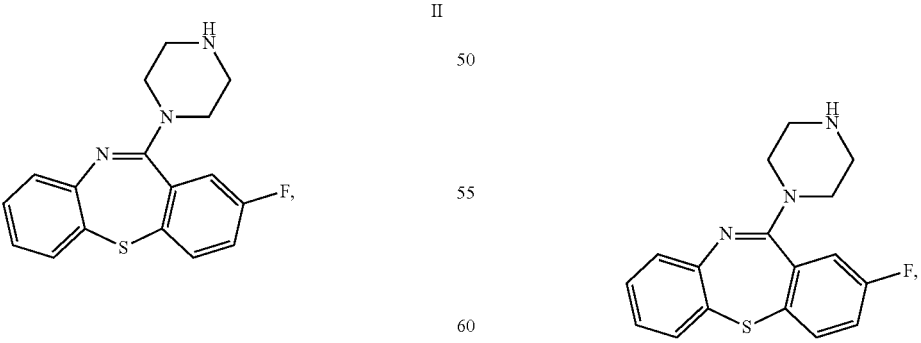

and pharmaceutically acceptable salts thereof, wherein Z is H, —C(=O)—$R^1$, —C(=O)$OR^1$, —C(=O)$OCH_2$, —CH($R^1$)—NHC(=O)$R^2$, —C(=O)$OCHR^2OC$(=O)$R^3$, —$CR^1$=$CR^2$ or —CH=CHC(=O)$R^4$, wherein $R^1$, $R^2$, $R^3$ and $R^4$ are each independently at each occurrence alkyl, cycloalkyl, aryl, heteroaryl or heterocycloalkyl or are as further described herein.

Specifically provided herein is a compound of Formula I wherein Z is H of Formula II:

II referred to herein as 2-fluoro-11-(piperazin-1-yl)dibenzo[b,f][1,4]thiazepine, and pharmaceutically acceptable salts thereof.

The compounds disclosed herein can be prepared by processes described herein by those skilled in the art of organic synthesis. The compounds can be synthesized using the methods described herein, using synthetic methods known in the art of synthetic organic chemistry, or variations thereon as appreciated by those skilled in the art. The starting materials and precursors used in the processes described herein are either commercially available, or readily prepared by established organic synthesis methods, or as described herein. It will be understood by those skilled in the art of organic synthesis that the functionality present on various portions of the molecule must be compatible with the reagents and reactions proposed. Such restrictions to the substituents that are compatible with the reaction conditions will be readily apparent to those skilled in the art and alternate methods should then be used.

As shown in Scheme 1, an amide compound of the present invention (formula 1-3) can be prepared by reacting the compound of Example 1 herein with an acid or acid derivative 1-2 (wherein $X^1$ is OH or a leaving group such as bromo, chloro, 4-nitrophenoxy, $OC(=O)R^1$, and the like; and $R^1$ can be alkyl, cycloalkyl, aryl, heteroaryl, heterocycloalkyl, and the like) under appropriate conditions known to those skilled in art of organic synthesis.

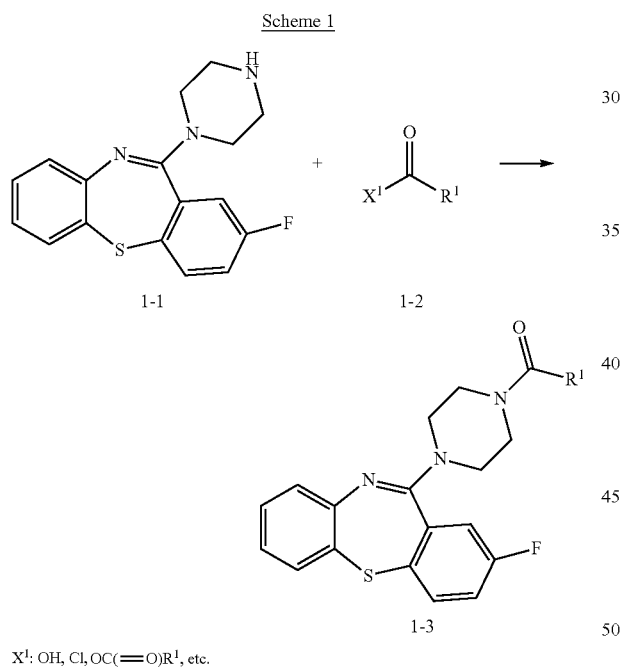

$X^1$: OH, Cl, $OC(=O)R^1$, etc.

For example, coupling of the amine compound 2-fluoro-11-(piperazin-1-yl)dibenzo[b,f][1,4]thiazepine 1-1 to an acid compound 1-2 (wherein $X^1$ is OH) can be carried out by a conventional amide bond formation method such as using a coupling reagent. Various suitable coupling reagents can be used to facilitate the coupling reaction of amide-bond formation. Those skilled in the art will readily recognize such coupling reagents. Some non-limiting examples of suitable coupling reagents include, but are not limited to, benzotriazole-containing coupling reagents such as N-hydroxybenzotriazole (HOBt), benzotriazol-1-yloxytris(dimethylamino)phosphonium hexafluorophosphate (BOP), and 2-(1H-benzotriazol-1-yl)-1,1,3,3-tetramethyluronium hexafluorophosphate (HBTU); an azabenzotriazole-containing reagent such as O-(7-azabenzotriazole-1-yl)-N,N,N'N'-tetramethyluronium hexafluorophosphate (HATU); and dicarboimides such as 1-ethyl-3-(3-dimethylaminopropyl)-carbodiimide (EDC), and dicyclohexyl carbodimide (DCC). The coupling reaction can be carried out in a suitable organic solvent. Some suitable organic solvents include polar organic solvents such as an alcohol (such as methanol, ethanol or isopropanol), or tetrahydrofuran (THF). Some suitable organic solvents include aprotic solvents. Some suitable organic solvents include polar aprotic organic solvent such as N,N-dimethylformamide (DMF), tetrahydrofuran (THF), dimethylsulfoxide (DMSO) or methylene chloride. The coupling reaction can be carried out in the presence of a suitable base and at a suitable temperature for a time sufficient to afford the amide compound 1-3. Suitable bases include organic bases such as tertiary amines (e.g., triethylamine ($Et_3N$ or TEA), diisopropylethylamine ($iPr_2NEt$ or DIPEA) and/or dimethylaminopyridine (DMAP)). In some embodiments, the reaction mixture is heated to an elevated temperature (i.e., above the room temperature). In some embodiments, the reaction mixture is heated to a temperature of about 40° C., about 50° C., about 60° C., about 70° C., about 80° C., about 90° C., about 100° C., about 110° C., about 120° C., about 130° C., about 140° C., about 150° C., or about 160° C. The reaction progress can be monitored by conventional methods such as TLC or NMR.

Alternatively, the acid 1-2 (wherein $X^1$ is OH) can be converted to a more reactive acid derivative 1-2 (wherein $X^1$ is bromo, chloro, 4-nitrophenoxy, $OC(=O)R^1$, and the like) such as an acid chloride, ester, a (mixed) anhydride, and the acid derivative can be optionally separated. The acid derivative can further react with 2-fluoro-11-(piperazin-1-yl)dibenzo[b,f][1,4]thiazepine 1-1 to form the amide 1-3 under suitable conditions such as in the presence of a suitable base (e.g., triethylamine or pyridine).

As shown in Scheme 2, a carbamate compound of the present invention (formula 2-3) can be synthesized by reacting the compound of Example 1 herein, 2-1) with a chloroformate 2-2 (wherein $R^1$ can be alkyl, arylalkyl, and the like).

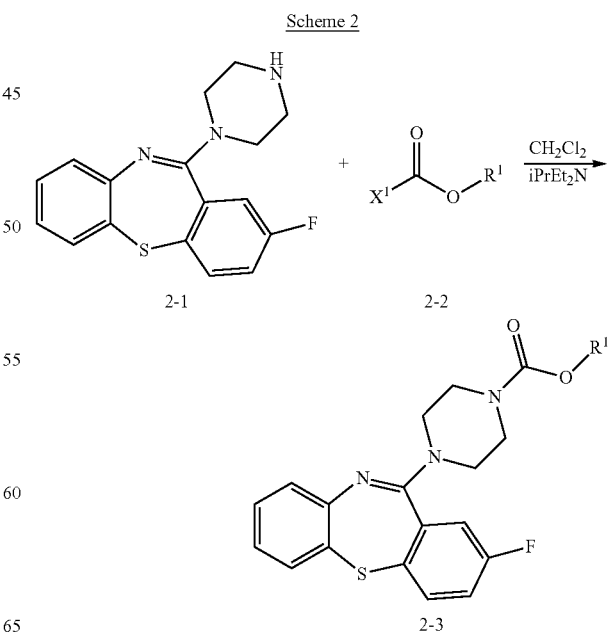

The reaction of scheme 2 can be carried out in a suitable organic solvent such as a polar aprotic organic solvent (e.g., methylene chloride) and in the presence of a suitable base such as a tertiary amine (e.g., triethylamine (Et₃N or TEA), diisopropylethylamine (iPr₂NEt or DIPEA), pyridine, and/or dimethylaminopyridine (DMAP)).

As shown in Scheme 3, a carbamate compound of the present invention (formula 3-5) can be synthesized via 4-nitrophenyl carbonate intermediate 3-3.

4-Nitrophenyl chloroformate 3-1 can be reacted with an alcohol 3-2 in a suitable organic solvent such as a polar aprotic organic solvent (e.g., chloroform) and in the presence of a suitable base such as a tertiary amine (e.g., triethylamine (Et₃N or TEA), diisopropylethylamine (iPr₂NEt or DIPEA), pyridine, and/or dimethylaminopyridine (DMAP)) to form a 4-nitrophenyl carbonate intermediate 3-3. The intermediate 3-3 can be reacted with 2-fluoro-11-(piperazin-1-yl)dibenzo[b,f][1,4]thiazepine 3-4 in a suitable organic solvent such as a polar aprotic organic solvent (e.g., N,N-dimethylformamide or hexamethylphosphoramide) to form the carbamate 3-5.

ing a compound of Example 1 herein, (4-1) with a chloroformate 4-2 or a 4-nitrophenyl carbonate compound 4-3 (wherein $R^2$ can be H, methyl, and the like; and $R^3$ can be alkyl (e.g., methyl or ethyl), alkoxy, cycloalkyl, aryl, heteroaryl, heterocycloalkyl, and the like).

Scheme 4

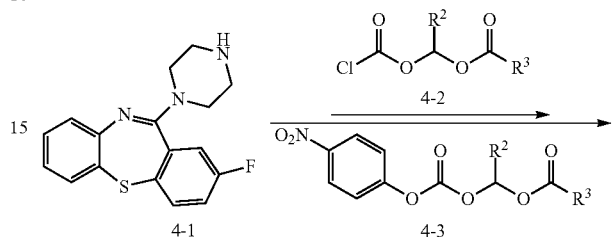

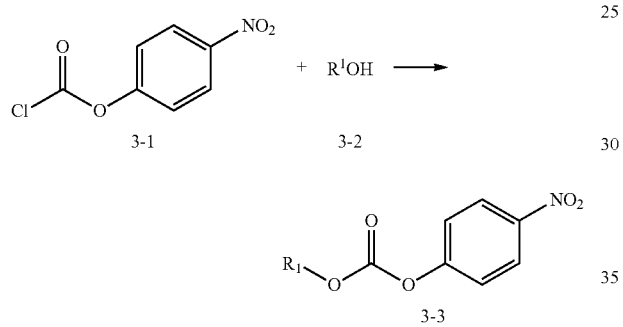

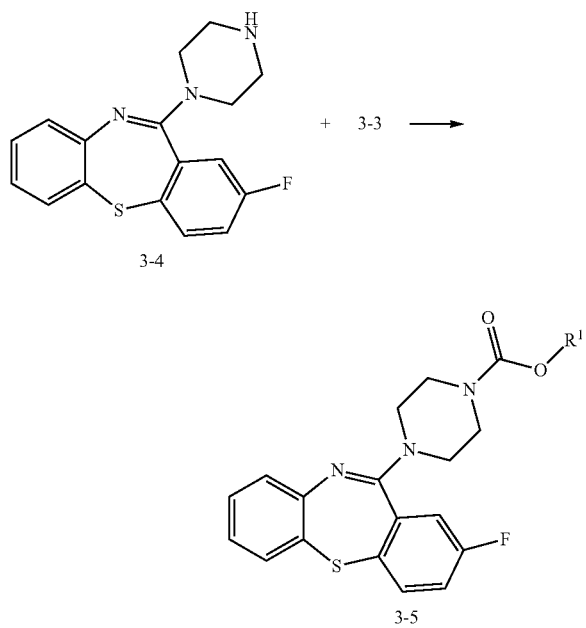

The reactions can be carried out in similar conditions to those described in Schemes 2 and 3. The chloroformates 4-2 can be made by those skilled in the art by using methods such as similar to one reported by Folkmann et al., Synthesis, 1990, 1159-1166. The nitrophenyl carbonates 4-3 can be made by those skilled in the art by using methods such as similar to one reported by Alexander and co-workers in J. Med. Chem., 1988, 31, 318-322. Each of the references is incorporated herein by its entirety.

As shown in Scheme 5, using a similar method to those reported by Lin et al., Biorganic and Medicinal Chemistry Letters, 1997, 7, 2909-2912, a carbamate compound of the present invention (formula 5-3) can be prepared by reacting a compound of Example 1 herein, 5-1 with a compound of formula 5-2 (wherein X is a leaving group such as iodo, bromo or chloro; $R^2$ can be H, methyl, and the like; and $R^3$ can be alkyl (e.g., methyl or ethyl), alkoxy, cycloalkyl, aryl, heteroaryl, heterocycloalkyl, and the like) in the presence of carbon dioxide and a suitable base such as cesium carbonate and in a suitable solvent such as N,N-dimethylformamide. Similarly, the compound of formula 5-5 can be prepared from a compound of Example 1, 5-1 and a compound of formula 5-4 (wherein $X^1$ is a leaving group such as iodo, bromo, chloro or 4-nitrophenylcarbonate) in the presence of carbon dioxide and a suitable base such as cesium carbonate.

As shown in Scheme 4, a carbamate compound of the present invention (formula 4-4) can be synthesized by react-

Scheme 5

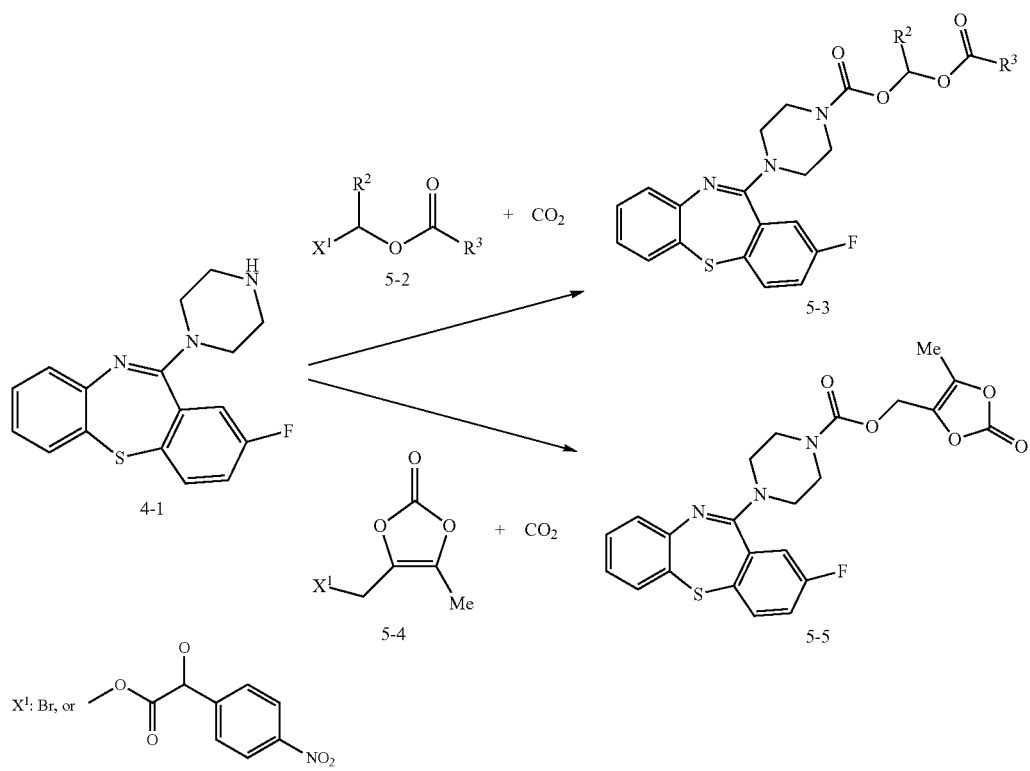

As shown in Scheme 6, an enamine compound of the present invention (formula 6-3) can be synthesized by reacting 2-fluoro-11-(piperazin-1-yl)dibenzo[b,f][1,4]thiazepine 6-1 with a ketone or aldehyde 6-2 (wherein $R^1$ can be H, alkyl, and the like; and $R^2$ can be H, alkyl, cycloalkyl, aryl, heteroaryl, heterocycloalkyl, and the like). The reaction can be carried out under a suitable condition such as in the presence of a catalyst such as p-toluenesulfonic acid and using a Dean-Stark trap to remove the water generated, and in a suitable organic solvent such as benzene or toluene. A novel enamine compound of the present invention (formula 6-5) can be synthesized by reacting 2-fluoro-11-(piperazin-1-yl)dibenzo[b,f][1,4]thiazepine 6-1 with an alkynone 6-4 (wherein $R^4$ can be alkyl, cycloalkyl, aryl, heteroaryl, heterocycloalkyl, and the like) under a suitable condition such as reflux in a suitable organic solvent such as ethyl acetate.

Scheme 6

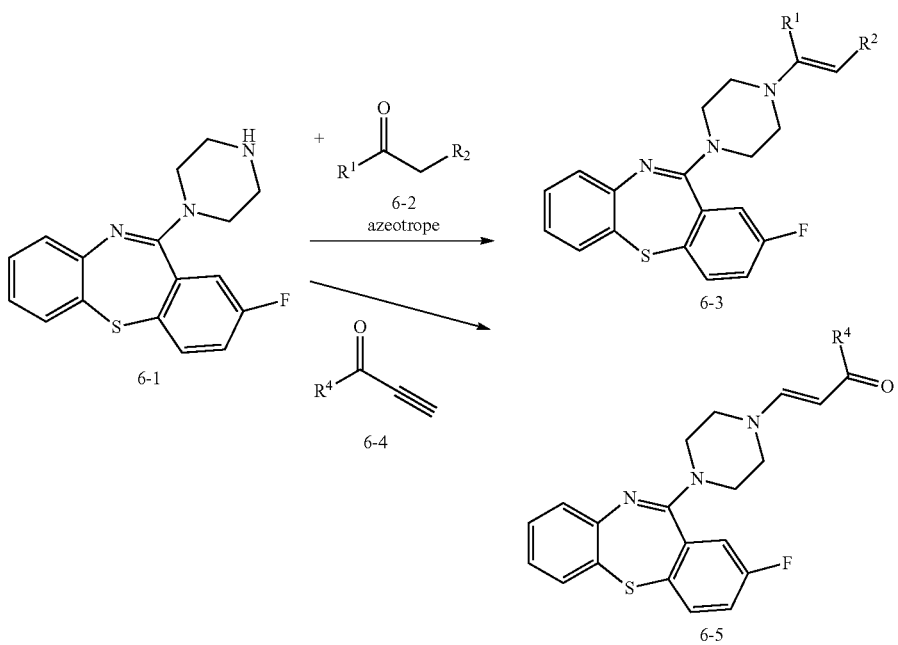

As shown in Scheme 7, a novel Mannich-base-type compound of the present invention (formula 7-4) can be prepared by reacting a compound of Example 1 herein, 7-1 with an aldehyde 7-2 (wherein $R^1$ can be H, alkyl, cycloalkyl, aryl, heteroaryl, heterocycloalkyl, and the like) and a nucleophile such as an amide 7-3 (wherein $R^2$ can be alkyl, cycloalkyl, aryl, heteroaryl, heterocycloalkyl, and the like) under suitable conditions such as reflux. For example, 2-fluoro-11-(piperazin-1-yl)dibenzo[b,f][1,4]thiazepine, formaldehyde aqueous solution and an amide 7-3 can be heated to reflux in an alcohol solvent such as ethanol to form a compound of formula 7-4 wherein $R^1$ is H.

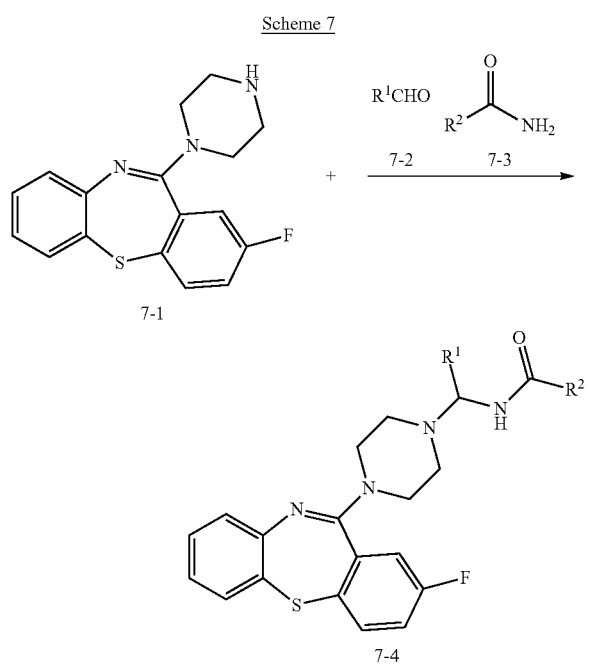

Scheme 7

It should noted that in all of the schemes described herein, if there are functional (reactive) groups present on a substituent group such as $R^1$, $R^2$, $R^3$, etc., further modification can be made if appropriate and/or desired. For example, a CN group can be hydrolyzed to afford an amide group; a carboxylic acid can be converted to an amide; a carboxylic acid can be converted to an ester, which in turn can be reduced to an alcohol, which in turn can be further modified. In another example, an OH group can be converted into another leaving group such as mesylate, which in turn is suitable for nucleophilic substitution, such as by CN. One skilled in the art will recognize further such modifications. Thus, a compound of formula I having a substituent that contains a functional group can be converted to another compound of formula I having a different substituent group.

The definitions set forth in this application are intended to clarify terms used throughout this application. The term "herein" means the entire application.

A variety of compounds in the present invention may exist in particular stereoisomeric forms. The present invention takes into account all such compounds, including cis- and trans isomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. When required, separation of the racemic material can be achieved by methods known in the art. The optically active forms of the compound of the invention may be prepared, for example, by chiral chromatographic separation of a racemate, by synthesis from optically active starting materials or by asymmetric synthesis based on the procedures described hereafter.

Where the compounds contain chiral centres, all individual optical forms such as enantiomers, epimers and diastereoisomers, as well as racemic mixtures of the compounds are within the scope of the invention.

Optical isomers can be obtained in pure form by standard procedures known to those skilled in the art, and include, but are not limited to, diastereomeric salt formation, kinetic resolution, and asymmetric synthesis. See, for example, Jacques et al., Enantiomers, Racemates and Resolutions (Wiley Interscience, New York, 1981); Wilen et al., Tetrahedron, 1977, 33, 2725; Eliel, Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in its entirety. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

It will also be appreciated that certain compounds of the present invention may exist as geometrical isomers, for example E and Z isomers of alkenes. A compound of the present invention, 2-fluoro-11-piperazin-1-yl-dibenzo[b,f][1,4]thiazepine, can in theory exist in (E) or (Z) forms, however (E)-2-fluoro-11-piperazin-1-yl-dibenzo[b,f][1,4]thiazepine has been the observed form. The invention nevertheless includes any geometrical isomer of a compound of the invention.

As used herein, the term "aryl" refers to an aromatic ring structure made up of from 5 to 14 carbon atoms. Ring structures containing 5, 6, 7, and 8 carbon atoms would be single-ring aromatic groups, for example, phenyl. Ring structures containing 8, 9, 10, 11, 12, 13, or 14 would be a polycyclic moiety in which at least one carbon is common to any two adjoining rings therein (for example, the rings are "fused rings"), for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls or cycloalkynyls. The terms ortho, meta and para apply to 1,2-, 1,3-, and 1,4-disubstituted benzenes, respectively. For example, the names 1,2-dimethylbenzene and ortho-dimethylbenzene are synonymous.

As used herein, "alkyl", "alkylenyl" or "alkylene" used alone or as a suffix or prefix, is intended to include both branched and straight-chain saturated aliphatic hydrocarbon groups having from 1 to 12 carbon atoms or if a specified number of carbon atoms is provided then that specific number would be intended. For example "$C_{1-6}$ alkyl" denotes alkyl having 1, 2, 3, 4, 5, or 6 carbon atoms. Examples of alkyl include, but are not limited to, methyl, ethyl, n-propyl, i-propyl, n-butyl, i-butyl, sec-butyl, t-butyl, pentyl, and hexyl, or any subset thereof. As used herein, "$C_{1-3}$ alkyl", whether a terminal substituent or an alkylene (or alkylenyl) group linking two substituents, is understood to specifically include both branched and straight-chain methyl, ethyl, and propyl.

As used herein, "alkoxy" or "alkyloxy" represents an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy, and propargyloxy, or any subset thereof. Similarly, "alkylthio" or "thioalkoxy" represent an alkyl group as defined above with the indicated number of carbon atoms attached through a sulfur bridge.

As used herein, "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is associated with an acidic or basic counter ion. For example, pharmaceutically acceptable salts include those derived from mineral acids such as, for example: hydrochloric acid, nitric acid, phosphoric acid, sulfuric acid, hydroiodic acid, nitrous acid, and phosphorous acid. Pharmaceutically acceptable salts may also be developed with organic acids including aliphatic mono dicarboxylates and aromatic acids. Other pharmaceutically acceptable salts include, but are not limited to, hydrochloride, sulfate, pyrosulfate, bisulfate, bisulfite, nitrate, phosphate, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid.

Compounds may exist in a number of tautomeric forms and references to compounds include all such forms. For the avoidance of doubt, where a compound can exist in one of several tautomeric forms and only one is specifically described or shown, all others are nevertheless embraced by the scope of this invention.

Compounds of the invention may include hydrates and solvates. It will also be understood that certain compounds of the present invention may exist in solvated, for example hydrated, as well as unsolvated forms. It will further be understood that the present invention encompasses all such solvated forms of the compounds of the invention.

Derivatives that are prodrugs of a compound are convertible in vivo or in vitro into parent compound. Typically, at least one of the biological activities of compound will be reduced in the prodrug form of the compound, and can be activated by conversion of the prodrug to release the compound or a metabolite of it. Some prodrugs are esters of the active compound (e.g., a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required.

Examples of such metabolically labile esters include, but are not limited to, those of the formula —C(═O)OR wherein R is: $C_{1-7}$alkyl (e.g., Me, Et, -nPr, -iPr, -nBu, -sBu, -iBu, tBu); $C_{1-7}$aminoalkyl (e.g., aminoethyl; 2-(N,N-diethylamino) ethyl; 2-(4-morpholino)ethyl); and acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl) ethyl-carbonyloxyethyl; 1-(benzoyloxy)ethyl; isopropoxycarbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl), or any subset thereof.

A compound of Formula I or Formula II, or a pharmaceutically acceptable salt thereof, or a pharmaceutical composition or formulation comprising a compound of Formula I or Formula II or a pharmaceutically acceptable salt thereof can be administered concurrently, simultaneously, sequentially or separately with another compound or compounds selected from the following:

(i) antidepressants such as, for example, amitriptyline, amoxapine, bupropion, citalopram, clomipramine, desipramine, doxepin, duloxetine, elzasonan, escitalopram, fluoxamine, fluoxetine, gepirone, imipramine, ipsapirone, maprotiline, nortriptyline, nefazodone, paroxetine, phenelzine, protriptyline, reboxetine, robaizotan, sertraline, sibutramine, thionisoxetine, tranylcypromaine, trazodone, trimipramine, venlafaxine, and equivalents and pharmaceutically active isomer(s) and/or metabolite(s) thereof;

(ii) atypical antipsychotics including, for example, quetiapine and pharmaceutically active isomer(s) and/or metabolite(s) thereof;

(iii) antipsychotics including, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perphenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and/or metabolite(s) thereof;

(iv) anxiolytics including, for example, alnespirone, azapirones, benzodiazepines, barbiturates, and equivalents and pharmaceutically active isomer(s) and/or metabolite(s) thereof. Exemplary anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(v) anticonvulsants including, for example, carbamazepine, valproate, lamotrogine, and gabapentin, and equivalents and pharmaceutically active isomer(s) and/or metabolite(s) thereof;

(vi) Alzheimer's therapies including, for example, donepezil, memantine, tacrine, and equivalents and pharmaceutically active isomer(s) and/or metabolite(s) thereof;

(vii) Parkinson's therapies including, for example, deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;

(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, and zomitriptan, and equivalents and pharmaceutically active isomer(s) and/or metabolite(s) thereof;

(ix) stroke therapies including, for example, abciximab, activase, citicoline, crobenetine, desmoteplase, repinotan, traxoprodil, and equivalents and pharmaceutically active isomer(s) and/or metabolite(s) thereof;

(x) urinary incontinence therapies including, for example, darafenacin, falvoxate, oxybutynin, propiverine, robalzotan, solifenacin, and tolterodine, and equivalents and pharmaceutically active isomer(s) and/or metabolite(s) thereof;

(xi) neuropathic pain therapies including, for example, gabapentin, lidoderm, and pregablin, and equivalents and pharmaceutically active isomer(s) and/or metabolite(s) thereof;

(xii) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;

(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, and zolpidem, and equivalents and pharmaceutically active isomer(s) and/or metabolite(s) thereof;

(xiv) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof;

(xv) $5HT_{1B}$ ligands such as, for example, compounds disclosed in WO99/05134, WO02/08212;

(xvi) mGluR2 agonists such as, for example, (1S,3R)-1-aminocyclopentane-1,3-dicarboxylic acid, (2S,3S,4S)alpha-(carboxycyclopropyl)glycine, and 3,5-dihydroxyphenylglycine or mGluR2 modulators such as those described in WO2004092135, WO2006071730, WO2008100715, WO2008150232 and WO2008150233;

(xvii) alpha 7 nicotinic agonists such as, for example, compounds disclosed in WO96/006098, WO97/030998, WO99/003859, WO00/042044, WO01/029034, WO01/160821, WO01/136417, WO02/096912, WO03/087102, WO03/087103, WO03/087104, WO04/016617, WO04/016616, and WO04/019947;

(xviii) chemokine receptor CCR1 inhibitors;

(xix) delta opioid agonists such as, for example, compounds disclosed in WO97/23466 and WO02/094794; and (xx) $5\text{-}HT_{1D}$ ligands, mGluR5 antagonists, NK1 receptor antagonists, and serotonin reuptake inhibitors.

Such combination products can employ a compound of Formula I or Formula II, or a pharmaceutically acceptable salt thereof, within the dosage range described herein and the other pharmaceutically active agent within approved dosage ranges and/or the dosage such as described in the publication reference. The appropriate dose regimen, the amount of each dose of an active agent administered, and the specific intervals between doses of each active agent will depend upon the subject being treated, the specific active agent being administered and the nature and severity of the specific disorder or condition being treated.

Compositions are intended to include the formulation of the active component or a pharmaceutically acceptable salt with a pharmaceutically acceptable carrier, and optionally other ingredients. For preparing pharmaceutical compositions, inert, pharmaceutically acceptable carriers can be either solid or liquid. For example, compositions can be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methylcellulose, sodium carboxymethyl cellulose, and other suspending agents known to the pharmaceutical formulation art.

Solid form compositions include powders, tablets, dispersible granules, capsules, cachets, and suppositories. A solid carrier can be one or more substances that may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is, thus, in association with it. Similarly, cachets are included.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. Methods of preparing dosage forms are disclosed in, for example, Remington's Pharmaceutical Sciences, Mack Publishing Company, Easton, Pa., 15th Edition, 1975.

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal, epidural, intraperitoneally, intrathoracically, intracerebroventricularly, and by injection into the joints) administration. The formulations may conveniently be presented in unit dosage form and may be prepared by any of the methods well known in the art of pharmacy.

A particular amount of a compound of Formula I or Formula II, or a pharmaceutically acceptable salt thereof, can be administered in an amount that ranges from about 0.25 mg/kg to about 10 mg/kg. More particularly, it is contemplated that a patient may be treated with about 0.25 mg/kg to about 5 mg/kg of 2-fluoro-11-(piperazin-1-yl)dibenzo[b,f][1,4]thiazepine or a pharmaceutically acceptable salt thereof. Most particularly, it is contemplated that a patient suffering with bipolar disorder may be treated with about 0.25 mg/kg to about 0.5 mg/kg of 2-fluoro-11-(piperazin-1-yl)dibenzo[b,f][1,4]thiazepine or a pharmaceutically acceptable salt thereof. Still more particularly it is contemplated that a patient suffering with a depressive phase of bipolar disorder may be treated with a lower amount in the range of about 0.25 mg/kg to about 0.5 mg/kg of 2-fluoro-11-(piperazin-1-yl)dibenzo[b,f][1,4]thiazepine or a pharmaceutically acceptable salt thereof whereas a patient suffering with a manic phase of bipolar disorder may be treated with a higher amount in the range of about 0.25 mg/kg to about 0.5 mg/kg of 2-fluoro-11-(piperazin-1-yl)dibenzo[b,f][1,4]thiazepine or a pharmaceutically acceptable salt thereof.

The amount of active ingredient that is combined with one or more excipients to produce a single dosage form will necessarily vary depending upon the host treated and the particular route of administration. The size of the therapeutically effective dose for therapeutic or prophylactic purposes of the active compound(s) will naturally vary from the guidance provided herein according to the nature and severity of the symptoms or conditions, the age and sex of the animal or patient and the route of administration, according to well known principles of medicine. A clinician may readily determine the effective amount by using numerous methods already known in the art and all such effective amounts are contemplated as being within the scope of the present invention.

Further provided herein are methods of treating, comprising the administration of an effective amount of a compound of Formula I or Formula II, or a pharmaceutically acceptable salt thereof, to a mammal, afflicted with at least one symptom or condition associated with a Psychiatric Disorder. In some embodiments, the Pyschiatric Disorder includes, but is not limited to: 1) Anxiety Disorders including, but not limited to, Panic Disorder Without Agoraphobia, Panic Disorder With Agoraphobia, Agoraphobia Without History of Panic Disorder, Specific Phobia, Social Phobia, Obsessive-Compulsive Disorder, Post-traumatic Stress Disorder, Acute Stress Disorder, Generalized Anxiety Disorder and Generalized Anxiety Disorder Due to a General Medical Condition; 2) Mood Disorders including, but not limited to, a) Depressive Disorders including, but not limited to, Major Depressive Disorder and Dysthymic Disorder, and b) Bipolar Depression and/or Bipolar mania including, but not limited to, Bipolar I Disorder including, but not limited to, those with manic, depressive or mixed episodes, and Bipolar II Disorder, c) Cyclothymic Disorder, and d) Mood Disorder Due to a General Medical Condition; and 3) Schizophrenia and other Psychotic Disorders including, but not limited to, Psychotic Disorder, Schizophreniform Disorder, Schizoaffective Disorder, Delusional Disorder, Brief Psychotic Disorder, Shared Psychotic Disorder, and Psychotic Disorder Due to a General Medical Condition, Dementia and other Cognitive Disorders. Examples of definitions of the above conditions and disorders can be found, for example, in the American Psychiatric Association: Diagnostic and Statistical Manual of Mental Disorders, Fourth Edition, Text Revision, Washington, D.C., American Psychiatric Association, 2000, herein referred to as "DSM-IV".

Particularly, provided herein are methods of treating, Bipolar I Disorder including, but not limited to, those with depressive, manic, or mixed episodes, and Bipolar II Disorder, Cyclothymic Disorder, and Mood Disorder Due to a General Medical Condition; and Schizophrenia comprising administering a therapeutically effective amount of a compound of Formula I, or a pharmaceutically acceptable salt thereof to a patient in need thereof. Most particularly, is provided methods of treating Bipolar Disorders including, but not limited to, those with depressive, manic, or mixed episodes, comprising administering a therapeutically effective amount of a compound of Formula I wherein Z is H, or a pharmaceutically acceptable salt thereof to a patient in need thereof.

In some embodiments, the symptoms and conditions include, but are not limited to, anxiety, agitation, hostility, panic, an eating disorder, an affective symptom, a mood symptom, a negative and positive psychotic symptom commonly associated with psychosis and neurodegenerative disorders.

In a certain embodiment, a compound of Formula I, or a pharmaceutically acceptable salt thereof, is delivered to a mammal by administering a pro-drug of 2-fluoro-11-(piperazin-1-yl)dibenzo[b,f][1,4]thiazepine, or a pharmaceutically acceptable salt thereof. Non-limiting examples of such pro-drugs can be found in embodiments in the current application when Z is $-C(=O)-R^1$, $-C(=O)OR^1$, $-C(=O)OCH_2$, $-CH(R^1)-NHC(=O)R^2$, $-C(=O)OCHR^2OC(=O)R^3$, $-CR^1=CR^2$ or $-CH=CHC(=O)R^4$, wherein $R^1$, $R^2$, $R^3$ and $R^4$ are each independently at each occurrence alkyl, cycloalkyl, aryl, heteroaryl or heterocycloalkyl or are as further described herein.

The term "treating" within the context of the present invention encompasses the administration of a therapeutically effective amount of a compound of the present invention to mitigate or inhibit either a pre-existing disease state, acute or chronic, or a recurring symptom or condition. Also encompassed are prophylactic therapies for prevention of recurring conditions and continued therapy for chronic disorders.

The term "mammal" refers to any warm-blooded animal, such as a human. In some embodiments, the mammal is in need of treatment because it is suffering from or prone to developing one or more of the symptoms, diseases, or disorders mentioned herein.

The term "administering" includes administering the pharmaceutically active ingredient or a pro-drug thereof, which may convert upon administration to the pharmaceutically active ingredient.

One expected benefit of administering 2-fluoro-11-(piperazin-1-yl)dibenzo[b,f][1,4]thiazepine or a pharmaceutically acceptable salt thereof is the lesser incidence of at least one potential side effect such as, for example, somnolence, sedation, a cardiovascular side effect, or a side effect associated with D2 antagonists (e.g., movement disorders). It is further expected that prodrugs of 2-fluoro-11-(piperazin-1-yl) dibenzo[b,f][1,4]thiazepine or its pharmaceutically acceptable will provide a reduction in at least one gastrointestinal side effect.

Thus, it is contemplated that treatment with 2-fluoro-11-(piperazin-1-yl)dibenzo[b,f][1,4]thiazepine or a pharmaceutically acceptable salt thereof, will provide beneficial improvement by providing a compound having potent inhibition of the norepinephrine transporter (NET), moderate D2 receptor antagonism and reduced affinity at secondary targets (e.g., H1 or M1) relative to NET for treating Bipolar and related Mood conditions classified in DSM-IV codes 296 and the subdivisions thereof. Correspondingly, it is contemplated that compounds of Formula I, and particularly 2-fluoro-11-(piperazin-1-yl)dibenzo[b,f][1,4]thiazepine or a pharmaceutically acceptable salt thereof, will be useful for treating Bipolar and related Mood conditions however such conditions are classified in the future in DSM-V.

It is also contemplated that treatment with 2-fluoro-11-(piperazin-1-yl)dibenzo[b,f][1,4]thiazepine or a pharmaceutically acceptable salt thereof, will be useful for treating Anxiety conditions classified in DSM-IV codes 300 and the subdivisions thereof. Correspondingly, it is contemplated that compounds of Formula I, and particularly treatment with 2-fluoro-11-(piperazin-1-yl)dibenzo[b,f][1,4]thiazepine or a pharmaceutically acceptable salt thereof, will be useful for treating Anxiety conditions however such conditions are classified in the future in DSM-V.

It is further contemplated that treatment with 2-fluoro-11-(piperazin-1-yl)dibenzo[b,f][1,4]thiazepine or a pharmaceutically acceptable salt thereof, will be useful for treating Schizophrenic conditions classified in DSM-IV codes 295 and the subdivisions thereof. Correspondingly, it is contemplated that compounds of Formula I, and particularly treatment with 2-fluoro-11-(piperazin-1-yl)dibenzo[b,f][1,4]thiazepine or a pharmaceutically acceptable salt thereof, will be useful for treating Schizophrenic conditions however such conditions are classified in the future in DSM-V.

Intermediate Compounds:

Intermediate compounds of Formula (A), useful in the synthesis of compounds of Formula I or Formula II, are described in the examples and schemes herein.

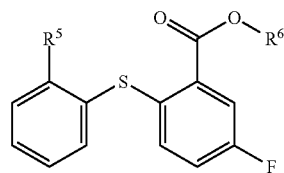

(A)

wherein $R^5$ is $NH_2$ or $NO_2$ and $R^6$ is H or $C_{1-4}$alkyl. In a more particular embodiment of a compound of Formula A, $R^5$ is $NH_2$ and $R^6$ is H, methyl or ethyl.

Still other intermediates of Formula (B), useful in the synthesis of compounds of Formula I or Formula II, are described in the examples and schemes herein.

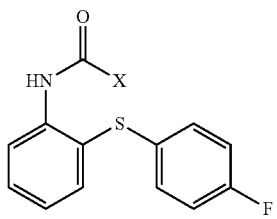

(B)

wherein X is Cl or phenoxy.

In order that the invention disclosed herein may be more efficiently understood, examples are provided below. It should be understood that these examples are for illustrative purposes only and are not to be construed as limiting the invention in any manner.

EXAMPLES

Example 1A 2-fluoro-11-(piperazin-1-yl)dibenzo[b,f][1,4]thiazepine

Scheme A shows one method of preparing 2-fluoro-11-(piperazin-1-yl)dibenzo[b,f][1,4]thiazepine (VI).

Scheme A

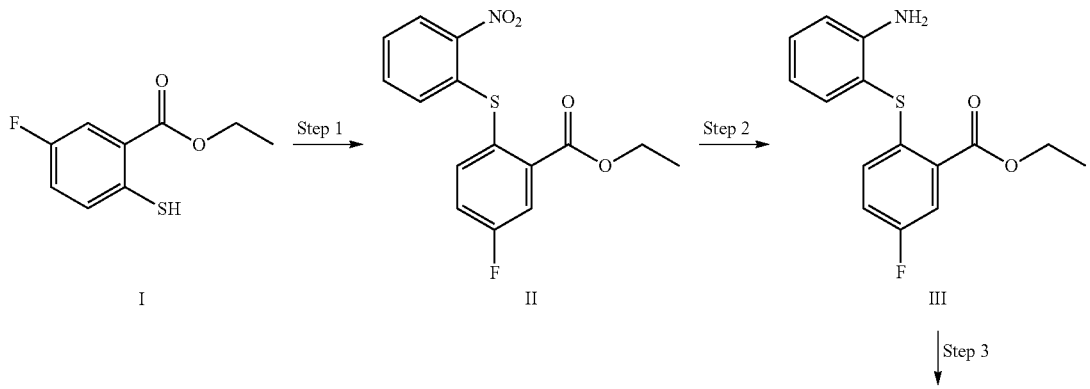

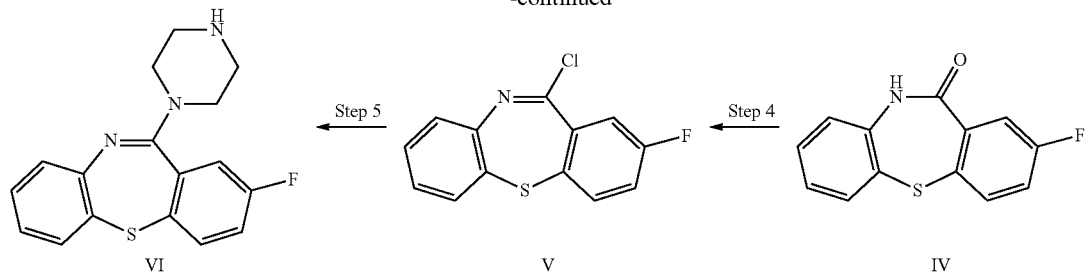

Thus, in a five-step process: 5-fluoro-2-mercapto-benzoic acid ethyl ester may be reacted with 1-fluoro-2-nitrobenzene to form 5-fluoro-2-(2-nitro-phenylsulfanyl)-benzoic acid ethyl ester; the ethyl ester may be converted to 5-fluoro-2-(2-amino-phenylsulfanyl)-benzoic acid ethyl ester; the aminophenyl compound may be cyclized to form 2-fluoro-10H-dibenzo[b,f][1,4]thiazepin-11-one, that may be converted to 11-chloro-2-fluoro-dibenzo[b,f][1,4]thiazepine, and that may be then reacted with piperazine to form the title compound.

Step 1:

To a solution of ethyl 5-fluoro-2-mercaptobenzoate (I) (25.0 g, 124.9 mmol) and 1-fluoro-2-nitrobenzene (13.2 mL, 124.9 mmol) in acetone (700 mL) was added $K_2CO_3$ (34.5 g, 249.7 mmol) at ambient temperature. The yellow suspension was heated to reflux (60° C.) for 5 hours. The reaction mixture was quenched with 1N HCl (500 mL), diluted with EtOAc (1000 mL) and filtered through a bed of diatomaceous earth. The aqueous layer was removed, the EtOAc layer was washed with 1N HCl (250 mL×2) and brine (200 mL×1), dried and the solvent removed under reduced pressure. The material was carried forward with no further purification to yield ethyl 5-fluoro-2-(2-nitrophenylthio)benzoate (II) (39.3 g, 95%) as a dark yellow solid. m/z (ES+) M+1=322.1; HPLC $t_R$=0.88 min. $^1$H NMR (300 MHz, DMSO-$d_6$): δ 1.09 (t, 3H, J=7.2 Hz), 4.16 (q, 2H, J=7.2 Hz), 7.07 (d, 1H, J=7.2 Hz), 7.40-7.75 (m, 5H), 8.20 (d, 1H, J=7.2 Hz).

Step 2:

To a solution of ethyl 5-fluoro-2-(2-nitrophenylthio)benzoate (II) (39.0 g, 121.4 mmol) in MeOH (530 mL) was added tin(II) chloride dihydrate (301 g, 1335.1 mmol) at ambient temperature. The milky yellow suspension was heated to reflux (65° C.) for 5 hours and then cooled. To the cooled mixture was added EtOAc (1000 mL) and solid $Na_2CO_3$ (141.5 g, 1335 mmol). While stirring vigorously, water was slowly added until foaming and tin salt formation ceased. Diatomaceous earth (500 g), was added and the reaction mixture stirred for 30 minutes and filtered. The aqueous layer was removed and the organic layer was washed with brine (500 mL×1), dried, and the solvent removed under reduced pressure. The material was carried forward with no further purification to yield the aniline ester (III) (17.7 g, 60.6%) as a pale yellow thick syrup. m/z (ES+) M+1=292.1; HPLC $t_R$=0.88 min. $^1$H NMR (300 MHz, DMSO-$d_6$): δ 1.34 (t, 3H, J=7.2 Hz), 4.35 (q, 2H, J=7.2 Hz), 5.36 (s, 2H), 6.57-6.70 (m, 2H), 6.85 (d, 1H, J=9.3 Hz), 7.18-7.35 (m, 3H), 7.70 (dd, 1H, 9.3 Hz).

Step 3:

To a solution of aniline ester (III) (17.6 g, 60.5 mmol) in toluene (300 mL) was added p-toluenesulfonic acid (11.6 g, 60.5 mmol) at ambient temperature under nitrogen. After heating the mixture at 110° C. for 16 hours, the reaction mixture was cooled to room temperature. The resulting cyclic lactam white precipitate was collected (3.9 g) and the filtrate concentrated under reduced pressure. The reaction mixture was triturated with MeOH (100 mL), the resulting cyclic lactam collected (5.8 g) and the filtrate again concentrated under reduced pressure. The material was purified by column chromatography over silica gel using 0-10% of MeOH in $CH_2Cl_2$ as an eluent to give cyclic lactam (1.8 g) as a white powder. The combined product batches gave the final cyclic lactam (IV) (11.2 g, 75%) as an off-white powder. m/z (ES+) M+1=246.1; HPLC $t_R$=0.71 min. $^1$H NMR (300 MHz, DMSO-$d_6$): δ 7.15 (t, 1H, J=9.3 Hz), 7.24 (d, 1H, J=9.3 Hz), 7.36 (m, 2H), 7.45 (dd, 1H, J=9.3 Hz), 7.55 (m, 2H), 10.78 (s, 1H).

Step 4:

A suspension of cyclic lactam (IV) (3.0 g, 12.2 mmol) and N,N-dimethylaniline (0.03 mL, 0.24 mmol) in $POCl_3$ (6.8 mL, 73.4 mmol) was heated at 125° C. for 2 hours. The reaction mixture was concentrated under reduced pressure. The residue was dissolved in $CH_2Cl_2$ (100 mL), washed with cold water (50 mL×2) and brine (50 mL×1), dried and the solvent removed under reduced pressure. The material was carried forward with no further purification to yield imino chloride (V) (3.1 g, 95%) as an amber syrup. m/z (ES+) M+1=264.1; HPLC $t_R$=0.95 min.

Step 5:

To a solution of imino chloride (V) (3.0 g, 11.5 mmol) in xylene (115 mL) was added piperazine (7.9 g, 92.2 mmol) at ambient temperature under nitrogen. After heating the mixture at 138° C. for 2 hours, the reaction was cooled to room temperature. The reaction was quenched with 2N HCl to pH 2.0, the acidic aqueous layer separated and washed with $CH_2Cl_2$ (2×100 mL). To the remaining acidic aqueous layer was added solid $K_2CO_3$ until pH 10 and EtOAc (200 mL) was added. The resulting emulsion was filtered through diatomaceous earth and the organic layer was separated. The organic layer was washed with brine (1×50 mL), dried over $MgSO_4$, filtered and concentrated under reduced pressure. The material was purified by column chromatography over silica gel using 0-5% of 7N $NH_3$/MeOH in $CH_2Cl_2$ as an eluent to give the title compound (2.0 g, 55%) as a pale yellow powder. m/z (ES+) M+1=314.2; HPLC $t_R$=0.50 min. $^1$H NMR (300 MHz, DMSO-$d_6$): δ 2.68 (m, 2H), 2.72 (m, 2H), 3.40 (m, 4H), 6.86 (t, 1H, J=8.1 Hz), 6.98 (d, 1H, J=8.1 Hz), 7.15-7.38 (br m, 4H), 7.58 (dd, 1H, J=8.1 Hz), 8.92 (br s, 1H).

Example 1B 2-fluoro-11-(piperazin-1-yl)dibenzo[b,f][1,4]thiazepine

Scheme B shows another contemplated method of preparing 2-fluoro-11-(piperazin-1-yl)dibenzo[b,f][1,4]thiazepine.

Scheme B

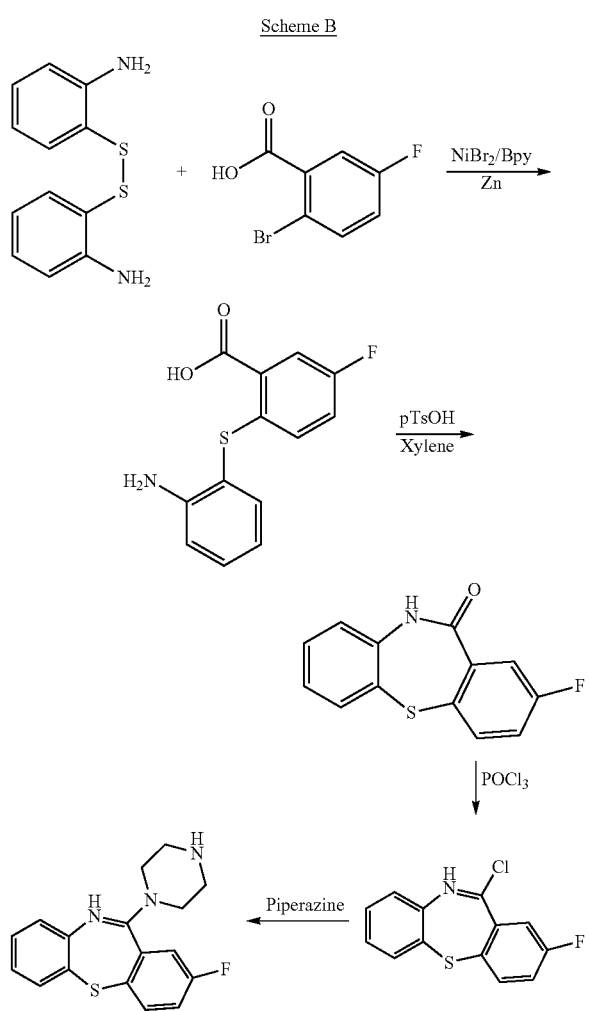

Thus, in a three-step process: 2,2'-disulfanediyldianiline may be reacted with 2-bromo-5-fluoro-benzoic acid, as shown, to form 2-(2-amino-phenylsulfanyl)-5-fluoro-benzoic acid; the benzoic acid may be cyclized, as shown, to form 2-fluoro-10H-dibenzo[b,f][1,4]thiazepin-11-one, that may be converted to 11-chloro-2-fluoro-dibenzo[b,f][1,4]thiazepine, and that may be reacted with piperazine to form the title compound.

Synthesis of 2-fluorodibenzo[b,f][1,4]thiazepin-11(10H)-one

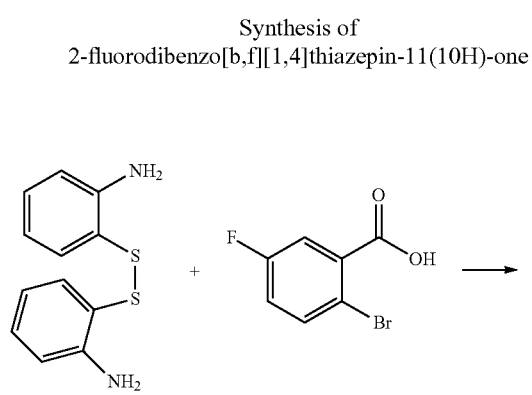

A suspension of nickel bromide (5 mmol, 1.09 g), bipyridyl (5 mmol, 0.78 g) and zinc dust (200 mmol, 13.08 g) in 200 mL dry acetonitrile was magnetically stirred, treated with 2,2'-disulfanediyldianiline (52 mmol, 12.92 g) and heated in an oil bath set at 75° C. for 30 min after reaching maximum internal temperature. At the end of this period the reaction mixture was treated with 2-bromo-5-fluorobenzoic acid (100 mmol, 21.90 g) in portions and stirred at 75° C. for 1 h and the oil bath was removed. The reaction mixture was cooled to the room temperature, transferred to a 1-neck flask and concentrated under reduced pressure. The resulting dark solid was suspended in 200 mL of methanol, cooled in ice and was treated with 100 mL of trifluoro acetic acid by adding through a dropping funnel. The resulting dark solution was stirred for 30 min until all the gas evolution stopped and filtered through a 3 cm pad of diatomous earth and the filtration pad was washed using a total of 400 mL methanol. The resulting gray suspension was refluxed for 1.5 h, cooled to the room temperature and stirred for 16 h and filtered to get a solid. The filtrate was evaporated and the resulting foam was treated with 300 mL 15% ammonium chloride solution and 500 mL ethyl acetate. The suspension was treated with solid sodium bicarbonate until pH 6-7 (16.8 g, 20 mmol). The resulting white suspension was stirred for 1 h and filtered. The solid residue was washed with 500 mL ethyl acetate. The organic layer from the filtrate was separated from the aqueous layer, dried over sodium sulfate and evaporated to yield an oil which was suspended in 200 mL ether, stirred for 1 h, filtered and the solid was washed with 100 mL ether. Combined solids were stirred with 250 mL hot methanol for 10 min and filtered to get the desired 2-(2-aminophenylthio)-5-fluorobenzoic acid as a solid. (17.42 g, 66%) MS (M+1) 264; 1H NMR (300 MHz, DMSO-$d_6$) δ ppm 3.06-3.45 (m, 1H) 4.84-5.70 (m, 2H) 6.53-6.70 (m, 2H) 6.82 (d, J=7.6 Hz, 1H) 7.09-7.25 (m, 2H) 7.26-7.36 (m, 1H) 7.66 (dd, J=9.5, 3.0 Hz, 1H).

A suspension of 2-(2-aminophenylthio)-5-fluorobenzoic acid (64.57 mmol, 17.51 g) in 500 mL xylenes was treated with p-toluenesulfonic acid monohydrate (64.57 mmol, 12.2 g) and heated. Additional 200 mL xylene was added and heating was continued with azeotropic removal of water for 16 h. The resulting pink reaction mixture was cooled to the room temperature and added to 300 mL water. After stirring for 15 min the solid removed by filtration, washed with 3×100 mL water and dried in air for 4 h, and then under high vacuum for 20 h to obtain 2-fluorodibenzo[b,f][1,4]thiazepin-11 (10H)-one as a off white solid (11.6 g, 73%); MS (M+1) 246; $^1$H NMR (300 MHz, DMSO-$d_6$) δ ppm 7.16 (t, 1H) 7.24 (d, J=7.2 Hz, 1H) 7.29-7.42 (m, 2H) 7.47 (dd, J=9.3, 2.9 Hz, 1H) 7.52-7.71 (m, 2H) 10.47-11.20 (m, 1H), MS 081119 M+1 246 (0.72).

2-Fluoro-11-(piperazin-1-yl)dibenzo[b,f][1,4]thiazepine may be prepared from 2-fluorodibenzo[b,f][1,4]thiazepin-11 (10H)-one as described in Steps 4 and 5 of the process of Example 1a.

Example 1C 2-fluoro-11-(piperazin-1-yl)dibenzo[b,f][1,4]thiazepine

Scheme C shows another contemplated method of preparing 2-fluoro-11-(piperazin-1-yl)dibenzo[b,f][1,4]thiazepine.

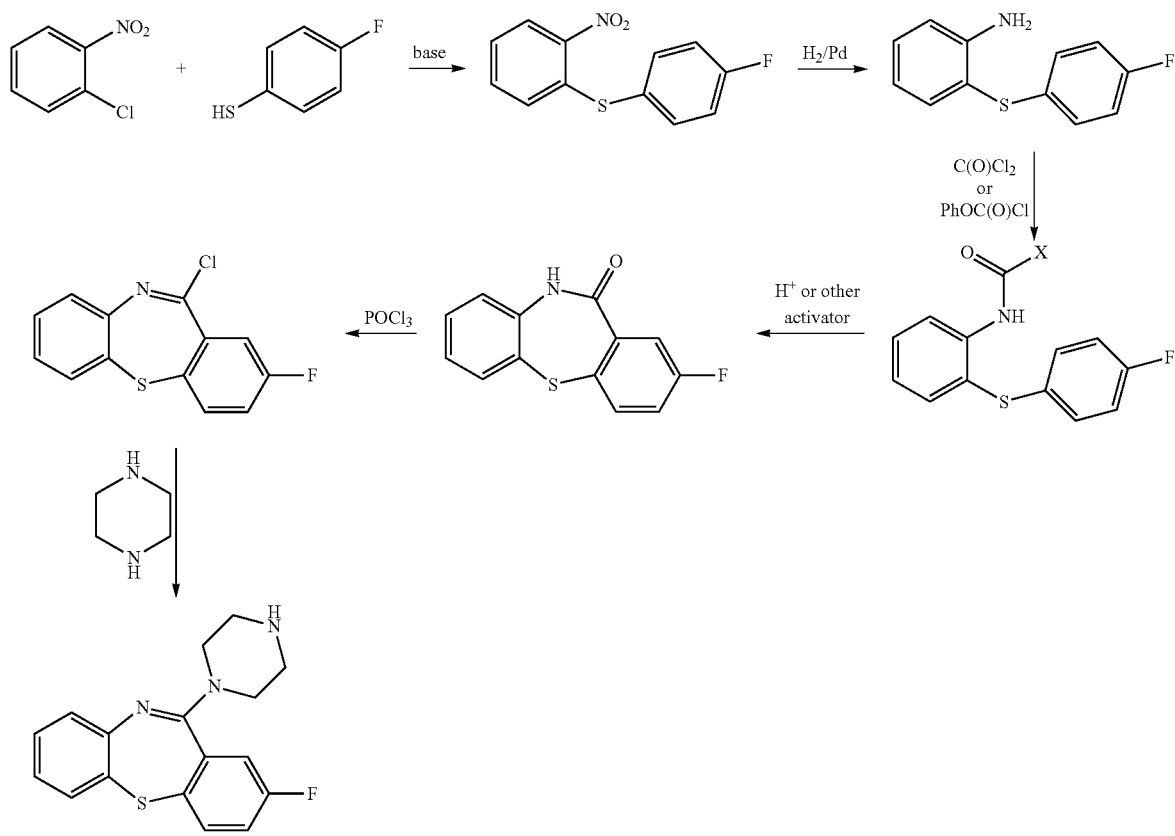

where X = Oph, Cl

Thus, 1-chloro-2-nitrobenzene may be reacted with 4-fluorobenzenethiol in the presence of a base to form 1-nitro-2-phenylsulfanyl-(4-fluorobenzene). The nitrofluorobenzene may be reduced to 1-amino-2-phenylsulfanyl-(4-fluorobenzene) which can converted (for example, as shown) to [2-(4-fluoro-phenylsulfanyl)-phenyl]-carbamic acid phenyl ester. Such an ester may be cyclized as shown to form 2-fluoro-10H-dibenzo[b,f][1,4]thiazepin-11-one, that may be converted to 11-chloro-2-fluoro-dibenzo[b,f][1,4]thiazepine, which can then be reacted with piperazine to form the title compound.

Example 1D 2-fluoro-11-(piperazin-1-yl)dibenzo[b,f][1,4]thiazepine

Scheme D shows yet another contemplated method of preparing 2-fluoro-11-(piperazin-1-yl)dibenzo[b,f][1,4]thiazepine.

Scheme D

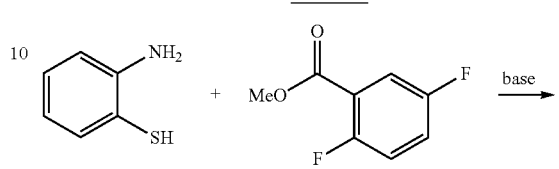

-continued

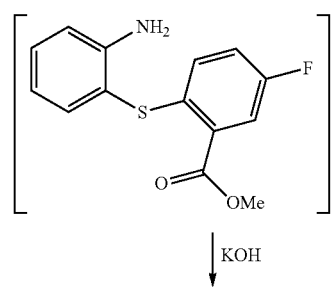

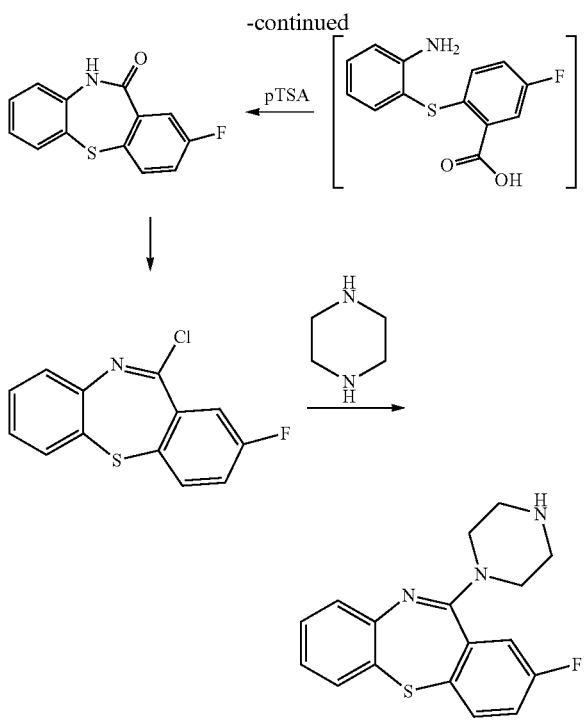

Thus, 2-aminobenzenethiol may be reacted with 2,5-difluoro-benzoic acid methyl ester to form a 2-[(E)-2-amino-1-eth-(E)-ylidene-but-2-enylsulfanyl]-5-fluoro-benzoic acid methyl ester intermediate that can be converted by treatment with alkali to 2-[(E)-2-amino-1-eth-(E)-ylidene-but-2-enylsulfanyl]-5-fluoro-benzoic acid. The benzoic acid can be cyclized to form 2-fluoro-10H-dibenzo[b,f][1,4]thiazepin-11-one, that may be converted to 11-chloro-2-fluoro-dibenzo[b,f][1,4]thiazepine, that may be further reacted with piperazine to form the title compound.

Example 2

1-(4-(2-fluorodibenzo[b,f][1,4]thiazepine-11-yl)piperazin-1-yl)ethanone

The compound of Formula I where Z is —C(=O)R$^1$ and R$^1$ is methyl was prepared as follows. To a solution of 2-fluoro-11-(piperazin-1-yl)dibenzo[b,f][1,4]thiazepine VI (see Scheme A) (0.05 g, 0.16 mmol) and triethylamine (0.05 mL, 0.32 mmol) in DCM (3 mL) was added acetyl chloride (0.02 mL, 0.32 mmol) dropwise at 0° C. under nitrogen. After stirring the mixture at 0° C. for 1 hour, the solvent was removed under reduced pressure. The reaction mixture was triturated with ether (1×20 mL), the insolubles filtered off and the filtrate concentrated under reduced pressure to give 1-(4-(2-fluorodibenzo[b,f][1,4]thiazepine-11-yl)piperazin-1-yl)ethanone (0.05 g, 80%) as a very pale yellow powder. m/z (ES+) M+1=356.0; HPLC $t_R$=0.64 min. $^1$H NMR (300 MHz, DMSO-d$_6$): δ 2.03 (s, 3H), 3.35-3.61 (br m, 8H), 6.90 (t, 1H, J=7.8 Hz), 7.01 (d, 1H, J=7.8 Hz), 7.22 (t, 1H, J=7.8 Hz), 7.31-7.40 (br m, 3H), 7.60 (dd, 1H, J=5.7 Hz).

Example 3 ethyl-4-(2-fluorodibenzo[b,f][1,4]thiazepine-11-yl)piperazin-1-carboxylate

The compound of Formula I where Z is —C(=O)OR$^6$ and R$^6$ is ethyl was prepared as follows. To a solution of 2-fluoro-11-(piperazin-1-yl)dibenzo[b,f][1,4]thiazepine VI (see Scheme A) (0.05 g, 0.16 mmol) and triethylamine (0.05 mL, 0.32 mmol) in DCM (3 mL) was added ethyl carbonchloridate (ethyl chloroformate) (0.03 mL, 0.32 mmol) dropwise at 0° C. under nitrogen. After stirring the mixture at 0° C. for 1 hour, the solvent was removed under reduced pressure. The reaction mixture was triturated with ether (1×20 mL), the insolubles filtered off and the filtrate concentrated under reduced pressure to give ethyl-4-(2-fluorodibenzo[b,f][1,4]thiazepine-11-yl)piperazin-1-carboxylate (0.05 g, 76%) as a yellow powder. m/z (ES+) M+1=386.4; HPLC $t_R$=0.82 min. $^1$H NMR (300 MHz, DMSO-d$_6$): δ 1.19 (t, 3H, J=7.2 Hz), 3.09 (br s, 1H), 3.32-3.61 (br m, 7H), 4.07 (q, 2H, J=7.2 Hz), 6.92 (t, 1H, J=7.5 Hz), 7.02 (d, 1H, J=7.8 Hz), 7.22 (t, 1H, J=7.2 Hz), 7.30-7.42 (br m, 3H), 7.60 (dd, 1H, J=5.4 Hz).

Example 4 benzyl-4-(2-fluorodibenzo[b,f][1,4]thiazepine-11-yl)piperazin-1-carboxylate

The compound of Formula I where Z is —C(=O)OR$^6$ and R$^6$ is benzyl was prepared as follows. To a solution of 2-fluoro-11-(piperazin-1-yl)dibenzo[b,f][1,4]thiazepine VI (see Scheme A) (0.05 g, 0.16 mmol) and triethylamine (0.05 mL, 0.32 mmol) in DCM (3 mL) was added benzyl carbonchloridate (benzyl chloroformate) (0.03 mL, 0.32 mmol) dropwise at 0° C. under nitrogen. After stirring the mixture at 0° C. for 1 hour, the solvent was removed under reduced pressure. The reaction mixture was triturated with ether (1×20 mL), the insolubles filtered off and the filtrate concentrated under reduced pressure to give benzyl-4-(2-fluorodibenzo[b,f][1,4]thiazepine-11-yl)piperazin-1-carboxylate (0.06 g, 90%) as a pale yellow waxy solid. m/z (ES+) M+1=448.2; HPLC $t_R$=0.94 min. $^1$H NMR (300 MHz, DMSO-d$_6$): δ 3.33-3.59 (br m, 8H), 5.12 (s, 2H), 6.93 (t, 1H, J=7.5 Hz), 7.01 (d, 1H, J=7.8 Hz), 7.23 (t, 1H, J=7.2 Hz), 7.25-7.42 (br m, 8H), 7.60 (m, 1H).

Example 5

D2 Assays

In vitro experimental assays can generally be carried out as described herein. Briefly, CHO-K1 cells stably transfected with the dopamine D2s receptor can be used in the experiments and maintained in Ham's F12 culture medium supplemented with 2 mM L-glutamine, 10% FBS, and 500 μg/ml Hygromycin.

D2 Receptor Binding Assay:

The ability of test compounds to displace $^3$H-raclopride at the D2s receptor can be determined on membranes from D2s-transfected CHO cells (B$_{max}$ 13 pmol/mg protein). An assay can use a standard 96-well glass-fiber filter plate to retain radioligand bound by the receptor. Retained $^3$H can be determined in a TopCount scintillation plate counter following the addition of a liquid scintillant to each well. Compounds can be evaluated for their potency using competition curve analysis, resulting in calculated K$_i$ values. When this method was carried out generally as described herein with 2-fluoro-11-(piperazin-1-yl)dibenzo[b,f][1,4]thiazepine, one average result obtained showed D2 binding K$_i$ at about 11 nM.

D2 Receptor In Vitro Functional Assays:

GTPgS assay can be performed substantially as described by Lazareno, Methods in Molecular Biology, 1999, 106, 231-245. Antagonist activity of compounds can be determined by the ability of test compounds to block dopamine-stimulated [$^{35}$S]-GTPγS binding to cell membranes from D2s stably-transfected CHO cells. When this method was carried out generally as described therein, with 2-fluoro-11-(piperazin-1-yl)dibenzo[b,f][1,4]thiazepine, one average result obtained showed a GTPγS $IC_{50}$ at about 404 nM.

Example 6

D-Amphetamine-Induced Hyperlocomotor Activity (LMA)

Studies in vivo can be used to determine the antipsychotic effect and are generally carried out as follows. Briefly, D-Amphetamine-induced Hyperlocomotor Activity (LMA) in a Habituated Rat Model can be assessed in male Long Evans rats using a paradigm that includes a habituation phase followed by administration of 1 mg/kg D-amphetamine. Animals can be allowed to acclimatize to the testing room for 1 hour before being weighed and placed into activity chambers. Thirty minutes after LMA measurement is begun, animals can be briefly removed, dosed via the sub-cutaneous route (s.c.) with vehicle or test drug at different doses and returned to the chambers. After a further 30 minutes, animals can again be removed and dosed with vehicle or D-amphetamine at 1 mg/kg (s.c.). After returning the animals to the activity chambers, LMA can be assessed for a further 60 minutes. Haloperidol (0.1 mg/kg dissolved in $H_2O$) can be administered 15 minutes prior to D-amphetamine via the s.c. route. Statistical analysis can be made of total distance traveled after D-amphetamine administration using ANOVA and Tukey's post hoc analysis where appropriate. All values can be expressed as Mean and SD. When this method was carried out generally as described therein, 2-fluoro-11-(piperazin-1-yl)dibenzo[b,f][1,4]thiazepine showed activity at 30 mg/kg and at 60 mg/kg (sc).

Example 7

Conditioned Avoidance Responding (CAR) Assay

Male Long-Evans rats can be trained to traverse to the opposite side of a standard shuttle cage following presentation of an auditory and visual stimulus to avoid delivery of electric shock to the floor of the cage. Daily sessions can consist of up to 80 trials. If a shock is delivered, animals have the opportunity to escape the shock by traversing to the opposite side of the cage. Drug can be administered (via s.c. or p.o. route) 60 minutes prior to testing and the percentage of trials in which shock is avoided and escaped can be recorded. When this method was carried out generally as described therein, 2-fluoro-11-(piperazin-1-yl)dibenzo[b,f][1,4]thiazepine showed activity at 30 mg/kg and at 60 mg/kg (sc).

Example 8

Norepinephrine Uptake

An assay for measuring norepinephrine uptake can be carried out as described below. Briefly, test compounds can be evaluated in an 11-point $IC_{50}$ curve for their ability to inhibit uptake of a proprietary fluorescent substrate (dye) from Molecular Devices that mimics biogenic amine neurotransmitters. A stable population of HEK293F cells transfected with the human norepinephrine transporter (cultured in Freestyle 293 expression medium with 75 mg/ml hygromycin B) can be cryopreserved, then plated and used on the day of the assay. Cells can be at 60K/well; dye can be 7% (final) of the vendor-recommended reconstitution volume (100%). Compounds can be diluted 1:20 in buffer and incubated with the cells for 30 minutes prior to addition of the dye. In this fluorescence intensity assay, plates can be read after a 20 minute dye incubation to determine percent effect with respect to total signal (0.5% DMSO, final) and background signal (10 μM desipramine, final). The $IC_{50}$, half of the control response, can be converted to $K_i$ using the using the standard Cheng-Prusoff equation. When this method was carried out generally as described herein with 2-fluoro-11-(piperazin-1-yl)dibenzo[b,f][1,4]thiazepine, one average result obtained showed NET inhibition $K_i$ at about 10 nM.

Example 9

H1 Receptor Binding

The H1 receptor binding method can be carried out in accordance with De Backer et al., Biochem. Biophys. Res. Commun., 1993, 197(3), 1601. When this method was carried out generally as described therein with 2-fluoro-11-(piperazin-1-yl)dibenzo[b,f][1,4]thiazepine, one average result obtained showed H1 binding $K_i$ at about 7.1 nM.

Pharmacological data concerning the compound of Example 1 and other piperazin-1-yl-dibenzo[b,f][1,4]thiazepines is shown in the table below.

| Compound Name | hNET uptake HEK FLInt CR Mean Ki (M) | D2 Ant GTPγS IC50 | D2 Ant GTPγS Top Effect | D2 binding w/ NaCl Ki (nM) | H1 Hu Bind Mean Ki (M) |
|---|---|---|---|---|---|
| (Example 1) 2-Fluoro-11-piperazin-1-yl-dibenzo[b,f][1,4]thiazepine | 9.60E−09 | 4.00E−07 | 97 | 11 | 7.12E−09 |
| 11-Piperazin-1-yl-dibenzo[b,f][1,4]thiazepine | 2.40E−08 | 8.00E−07 | 89 | 37 | 3.33E−09 |
| 2-Chloro-11-piperazin-1-yl-dibenzo[b,f][1,4]thiazepine | 4.10E−08 | 3.50E−08 | 100 | 0.7 | 3.87E−09 |
| 2-Chloro-11-(4-methyl-piperazin-1-yl)-dibenzo[b,f][1,4]thiazepine | 5.10E−08 | 8.40E−09 | 100 | 0.49 | 1.52E−09 |
| 2-Fluoro-11-(4-methyl-piperazin-1-yl)-dibenzo[b,f][1,4]thiazepine | 5.90E−08 | 1.70E−07 | 100 | 1.1 | 1.82E−09 |

Various modifications of the invention, in addition to those described herein, will be apparent to those skilled in the art from the foregoing description. Such modifications are also intended to fall within the scope of the appended claims. Provisional application 60/074,417 and each mentioned reference, is incorporated herein by reference in its entirety.

What is claimed is:

1. A method of making 2-fluoro-11-(piperazin-1-yl)dibenzo[b,f][1,4]thiazepine, said method comprising:
   reacting 5-fluoro-2-mercapto-benzoic acid ethyl ester with 1-fluoro-2-nitrobenzene to form 5-fluoro-2-(2-nitro-phenylsulfanyl)-benzoic acid ethyl ester;
   converting 5-fluoro-2-(2-nitro-phenylsulfanyl)-benzoic acid ethyl ester to 5-fluoro-2-(2-amino-phenylsulfanyl)-benzoic acid ethyl ester;
   cyclizing 5-fluoro-2-(2-amino-phenylsulfanyl)-benzoic acid ethyl ester to form 2-fluoro-10H-dibenzo[b,f][1,4]thiazepin-11-one;
   converting 2-fluoro-10H-dibenzo[b,f][1,4]thiazepin-11-one to 11-chloro-2-fluoro-dibenzo[b,f][1,4]thiazepine, and
   reacting 11-chloro-2-fluoro-dibenzo[b,f][1,4]thiazepine with piperazine to form 2-fluoro-11-(piperazin-1-yl)dibenzo[b,f][1,4]thiazepine.

2. A method of making 2-fluoro-11-(piperazin-1-yl)dibenzo[b,f][1,4]thiazepine, said method comprising:
   reacting 1-chloro-2-nitrobenzene with 4-fluorobenzenethiol in the presence of a base to form 1-nitro-2-phenylsulfanyl-(4-fluorobenzene);
   reducing 1-nitro-2-phenylsulfanyl-(4-fluorobenzene) to 1-amino-2-phenylsulfanyl-(4-fluorobenzene);
   converting 1-amino-2-phenylsulfanyl-(4-fluorobenzene) to [2-(4-fluoro-phenylsulfanyl)-phenyl]-carbamic acid phenyl ester;
   cyclizing the ester to 2-fluoro-10H-dibenzo[b,f][1,4]thiazepin-11-one;
   converting 2-fluoro-10H-dibenzo[b,f][1,4]thiazepin-11-one to 11-chloro-2-fluoro-dibenzo[b,f][1,4]thiazepine, and
   reacting 11-chloro-2-fluoro-dibenzo[b,f][1,4]thiazepine with piperazine to form 2-fluoro-11-(piperazin-1-yl)dibenzo[b,f][1,4]thiazepine.

3. A method of making 2-fluoro-11-(piperazin-1-yl)dibenzo[b,f][1,4]thiazepine, said method comprising:
   reacting 2-aminobenzenethiol with 2,5-difluoro-benzoic acid methyl ester to form a 2-[(E)-2-amino-1-eth-(E)-ylidene-but-2-enylsulfanyl]-5-fluoro-benzoic acid methyl ester;
   converting 2-[(E)-2-amino-1-eth-(E)-ylidene-but-2-enylsulfanyl]-5-fluoro-benzoic acid methyl ester to 2-[(E)-2-amino-1-eth-(E)-ylidene-but-2-enylsulfanyl]-5-fluoro-benzoic acid by treatment with alkali;
   cyclizing 2-[(E)-2-amino-1-eth-(E)-ylidene-but-2-enylsulfanyl]-5-fluoro-benzoic acid to 2-fluoro-10H-dibenzo[b,f][1,4]thiazepin-11-one;
   converting 2-fluoro-10H-dibenzo[b,f][1,4]thiazepin-11-one to 11-chloro-2-fluoro-dibenzo[b,f][1,4]thiazepine, and
   reacting 11-chloro-2-fluoro-dibenzo[b,f][1,4]thiazepine with piperazine to form 2-fluoro-11-(piperazin-1-yl)dibenzo[b,f][1,4]thiazepine.

* * * * *